United States Patent
Schendel

(10) Patent No.: US 6,277,094 B1
(45) Date of Patent: *Aug. 21, 2001

(54) APPARATUS AND METHOD FOR DILATING LIGAMENTS AND TISSUE BY THE ALTERNATING INSERTION OF EXPANDABLE TUBES

(75) Inventor: Michael James Schendel, Andover, MN (US)

(73) Assignee: Medtronic, Inc., Minneapolis, MN (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/301,095

(22) Filed: Apr. 28, 1999

(51) Int. Cl.[7] .................................................. A61M 29/00
(52) U.S. Cl. ............................................................ 604/104
(58) Field of Search ................................ 604/104, 164, 604/96, 523, 264; 128/3; 606/108

(56) References Cited

U.S. PATENT DOCUMENTS

| | | | |
|---|---|---|---|
| 4,601,713 | * 7/1986 | Fuqua | 604/280 |
| 4,738,666 | 4/1988 | Fuqua | 604/280 |
| 4,862,891 | * 9/1989 | Smith | 606/191 |
| 4,863,476 | 9/1989 | Shepperd | 623/17 |
| 5,183,464 | 2/1993 | Dubrul et al. | 128/3 |
| 5,221,261 | 6/1993 | Termin et al. | 604/104 |
| 5,320,611 | 6/1994 | Bonutti et al. | 604/264 |
| 5,417,719 | 5/1995 | Hull et al. | 607/46 |
| 5,425,760 | 6/1995 | Rosenberg | 623/8 |
| 5,429,117 | 7/1995 | McNamara et al. | 600/104 |
| 5,441,515 | 8/1995 | Khosravi et al. | 606/194 |
| 5,454,364 | 10/1995 | Kruger | 600/114 |
| 5,468,248 | 11/1995 | Chin et al. | 606/192 |
| 5,749,889 | * 5/1998 | Bacich et al. | 606/198 |
| 5,891,091 | * 4/1999 | Teirstein | 604/104 |

* cited by examiner

Primary Examiner—Richard K Seidel
Assistant Examiner—Kevin Sirmons
(74) Attorney, Agent, or Firm—Banner & Witcoff, Ltd

(57) ABSTRACT

There is disclosed an apparatus and method for dilating the ligamentum flava or other soft tissue in the human body comprising a radially expandable dilator defining a first expandable tube and an offset tubular guide. A second expandable tube having an integral external guide cam is inserted into the opening of the first expandable tube and aligned with the slit in the first tube effecting radial expansion of the expandable dilator, thereby causing dilation of the ligamentum flava or other tissue. The dilation of the ligamentum flava or other tissue allowing insertion of larger medical leads or surgical instruments into the epidural space.

19 Claims, 5 Drawing Sheets

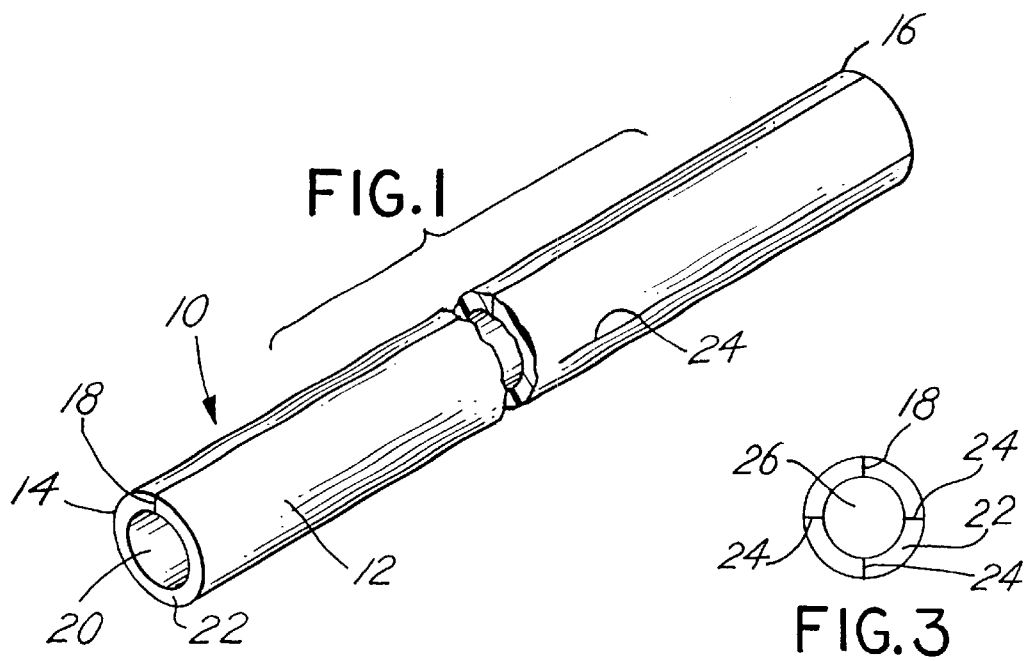
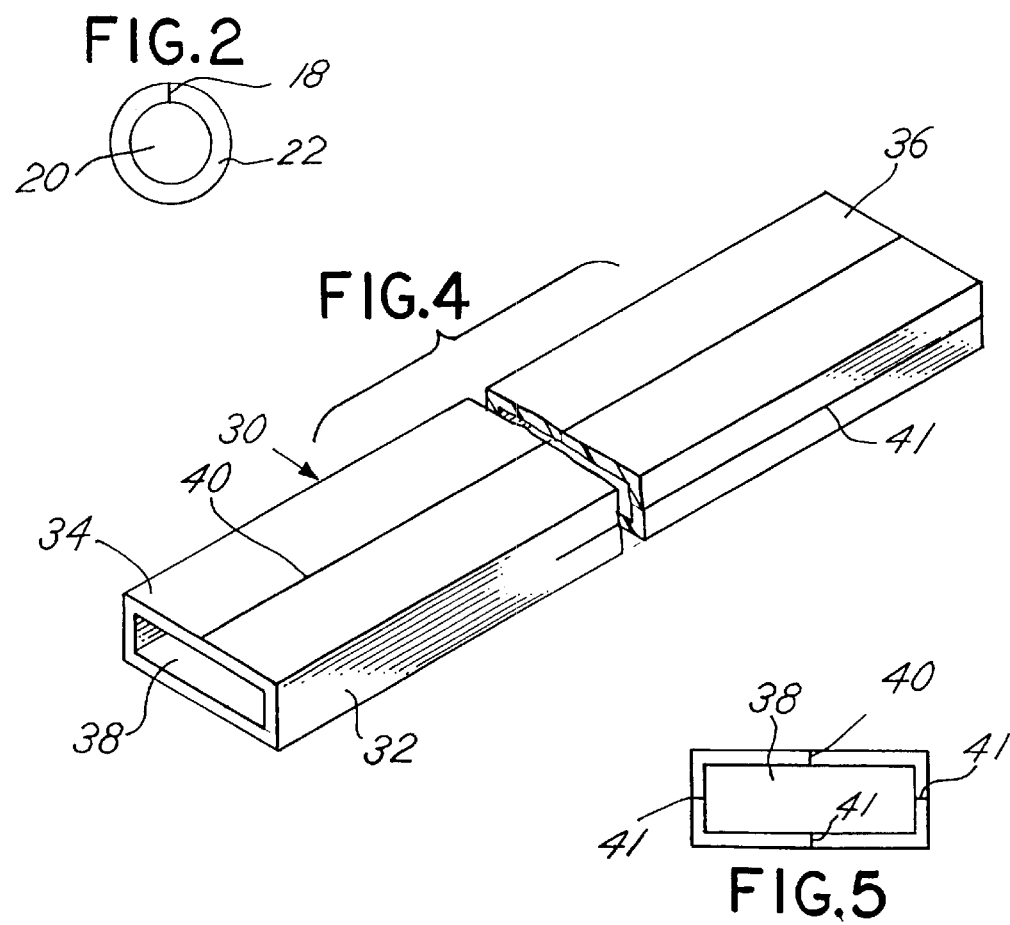

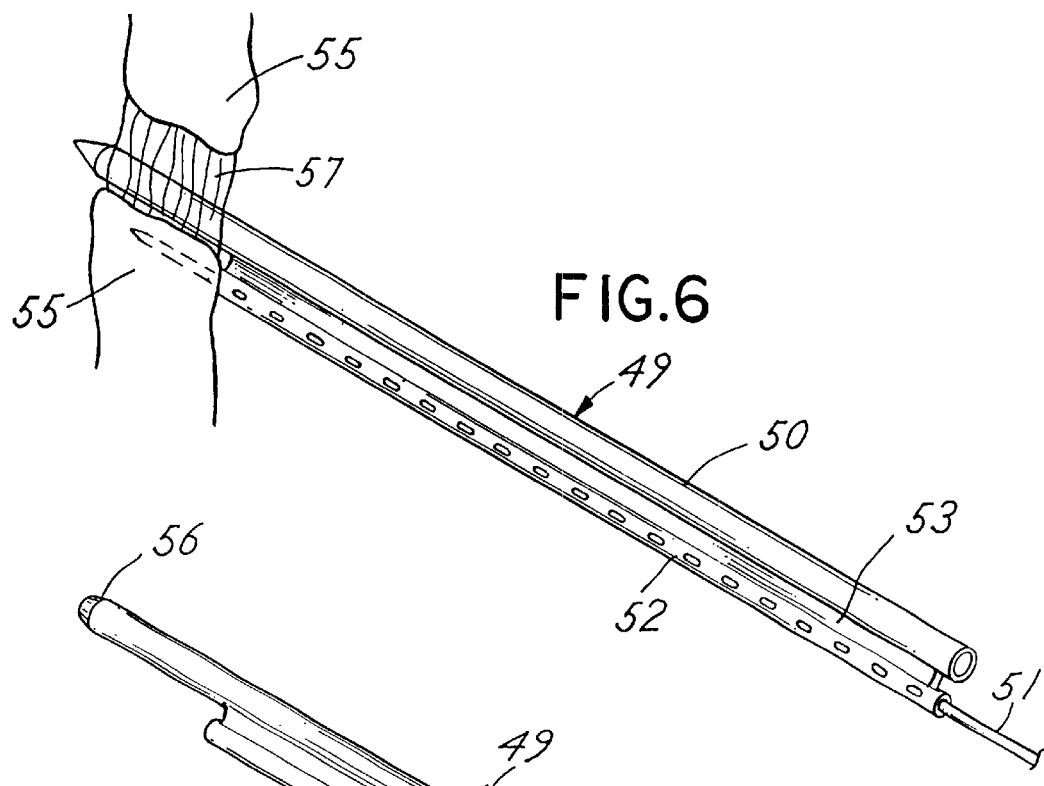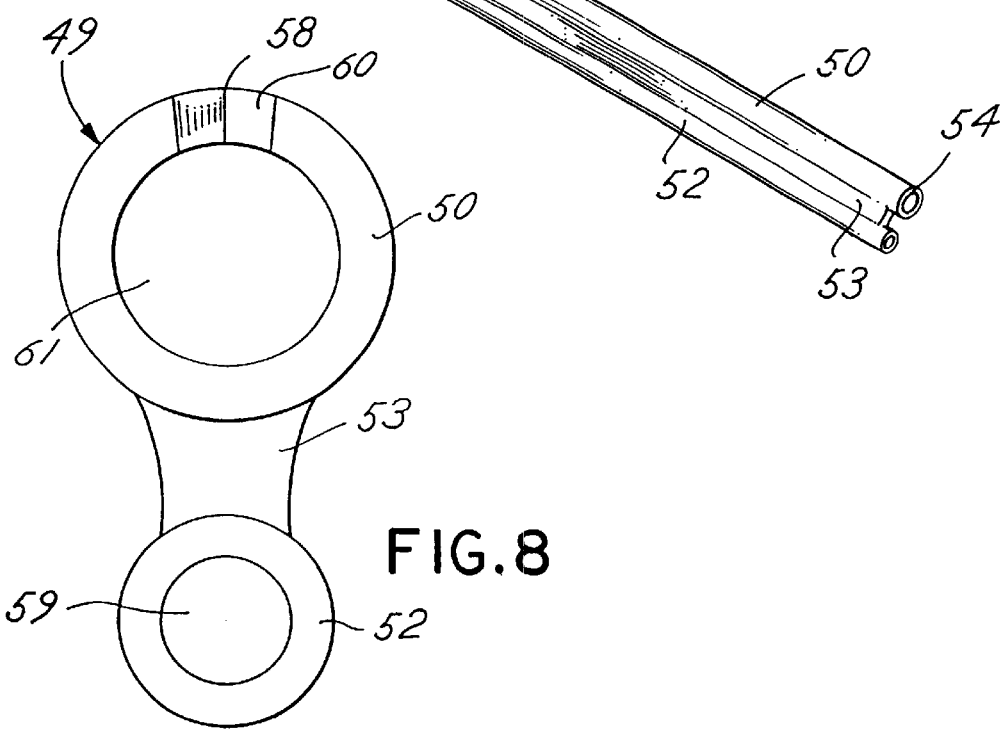

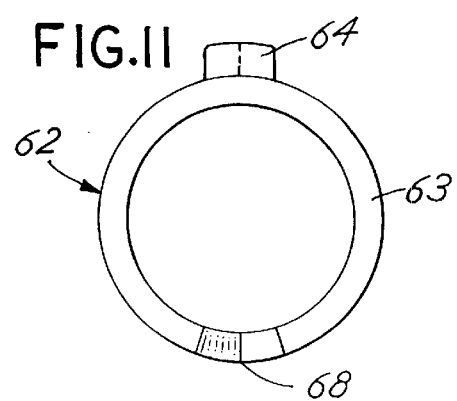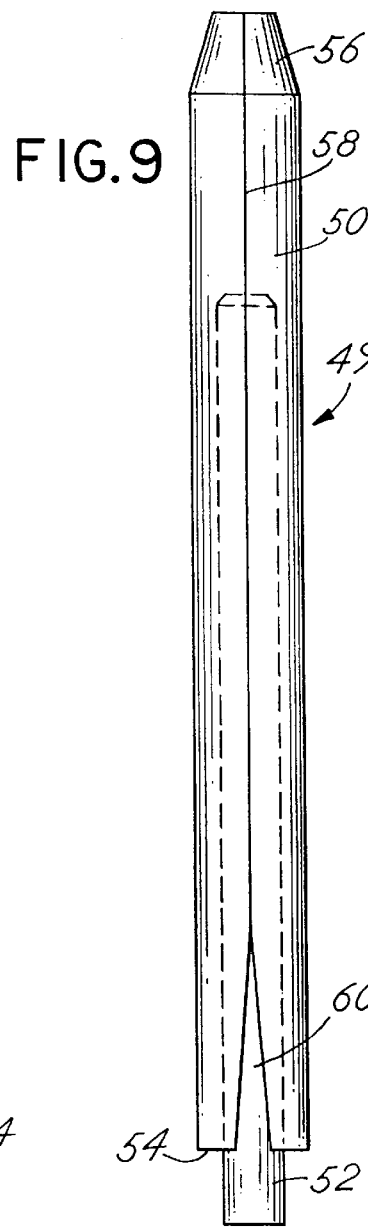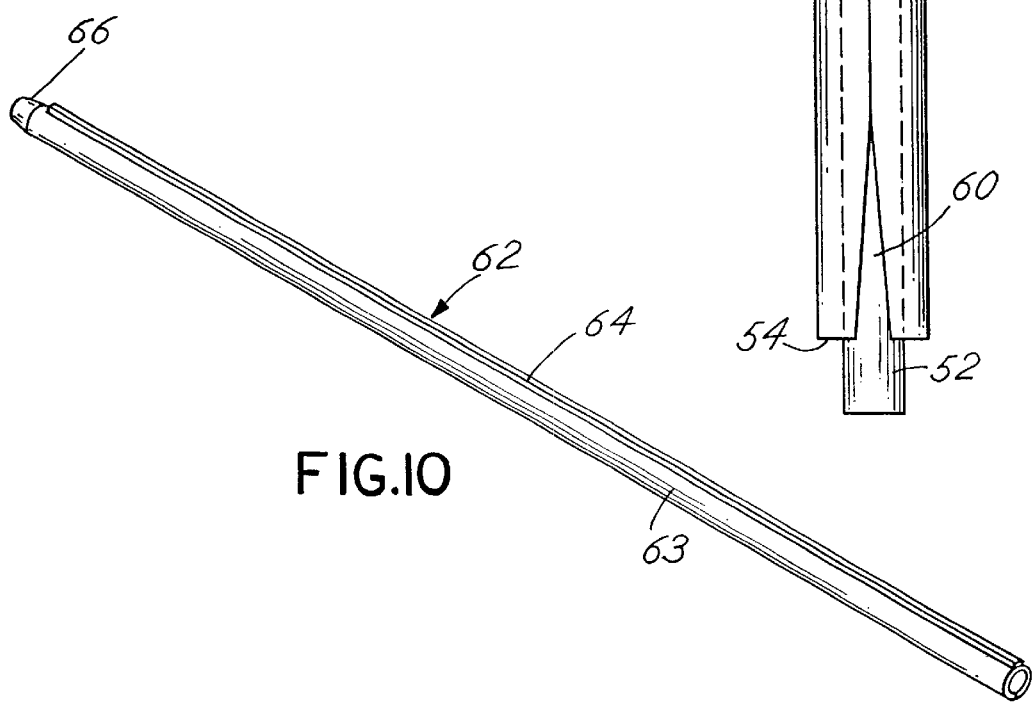

APPARATUS AND METHOD FOR DILATING LIGAMENTS AND TISSUE BY THE ALTERNATING INSERTION OF EXPANDABLE TUBES

BACKGROUND OF THE INVENTION

1. Field of the Invention

The present invention relates to percutaneous dilators and more particularly to an apparatus and method for dilating the ligamentum flava and other soft tissue by the alternating insertion of expandable tubes.

2. Description of the Related Art

Electrical stimulation of electrically excitable tissue such as the brain and/or nerve tissue of the spinal cord or peripheral nerve is an increasingly popular technique for treatment of pain or treatment of neural disorders. For example, medical leads having electrode contacts have been implanted near the spinal cord of the human body to provide pain relief for chronic intractable pain. A current technique for implanting a medical lead into the epidural space of the spinal column is a laminotomy which is a highly invasive technique requiring the cutting of the skin, tissue, ligamentum flava, and bone surrounding the epidural space. A more desirable and less invasive technique is to percutaneously implant a medical lead in the epidural space. This technique involves piercing a needle through the skin and tissue to the targeted area, thereby creating an access hole for the insertion of the medical lead. It is often desirable to implant larger leads which are more stable when implanted in the epidural space and provide better nerve fiber coverage for more effective pain reduction. An example of such leads are paddle leads as disclosed in U.S. Pat. No. 5,417,719. These larger leads, however, require a larger access hole and presently, these leads have been implanted by a laminotomy. A more efficient and equally effective method of increasing the access hole to the targeted area is through the use of dilators or similar expansion tubes. By using a dilator, the surrounding skin and tissue is expanded, thereby enlarging the access hole without doing a laminotomy. A related patent includes U.S. Pat. No. 5,183,464 which describes an expandable dilator for forming and enlarging percutaneous penetrations into hollow body organs, tissues or cavities. This patent, however, requires several components to effect expansion including, for example, a pair of coaxial cylinders, an outer sheath, and an inner rod. This patent also does not provide for the anchoring of the dilator at the targeted penetration area. Other background patents include U.S. Pat. No. 5,320,611 which describes an expandable cannula, and U.S. Pat. No. 4,738,666 which describes an expandable catheter. These patents are incorporated herein by reference.

SUMMARY OF THE INVENTION

The present invention overcomes the aforementioned disadvantages of the prior art. Accordingly, an object of the present invention is to provide for the implantation of larger diameter lead bodies percutaneously through the dilation of the small opening formed in the skin, ligamentum flava, or other soft tissue.

The present invention provides an apparatus and method for dilating the ligamentum flava and other soft tissue from a small puncture opening having a small diameter to a larger workable diameter wherethrough larger medical lead bodies, surgical instruments or medication can pass. The apparatus works by progressively dilating the opening from the skin to the targeted tissue. The dilation is accomplished by the alternating insertion of dilators and progressively larger diameter tubes.

In use, a needle is percutaneously inserted into the ligamentum flava or targeted cavity. An expandable tube or dilator is then inserted inside the lumen of the needle. The dilator includes a slit extending longitudinally across the length of the dilator and a plurality of slits at the distal end of the dilator to permit the expansion of the dilator. The needle is removed leaving the dilator in place at the targeted area. A larger diameter slotted or solid tube is then inserted inside the dilator effecting the expansion of the dilator which, in turn, expands the surrounding skin and tissue creating a larger access hole. The dilator is then removed leaving the larger diameter tube in place for the introduction of larger leads, such as paddle type leads, or surgical instruments. If desirable, an even larger opening can be made by simply repeating the previous steps using a slightly larger diameter dilator and a larger slotted or solid tube. This process may be repeated until the tube with the desired diameter is in position at the targeted insertion area.

As preferred and detailed below, the dilator includes an offset guide channel for receiving a guide wire which is drilled into the bone adjacent to the targeted area. The guide wire serves to anchor the dilator in the desired position. A second dilator having a slotted lumen and a guide cam extending along the length of the second dilator is inserted into the opening of the dilator with the offset guide channel. Through the alternating insertion of these dilators, the access hole can be enlarged while maintaining a fixed position of the dilator relative to the targeted area.

The full range of objects, aspects and advantages of the invention are only appreciated by a full reading of this specification and a full understanding of the invention. Therefore, to complete this specification, a detailed description of the invention and the preferred embodiments follow, after a brief description of the drawings.

BRIEF DESCRIPTION OF THE DRAWINGS

The preferred embodiments of the invention will be described in relation to the accompanying drawings. In the drawings, the following figures have the following general nature:

FIG. 1 is an isometric view of the dilator of the present invention.

FIG. 2 is an end view of the proximal portion of the dilator of FIG. 1.

FIG. 3 is an end view of the distal portion of the dilator of FIG. 1.

FIG. 4 is an isometric view of the rectangular dilator of the present invention.

FIG. 5 is an end view of the distal end of the dilator of FIG. 4.

FIG. 6 is an isometric view of an alternative embodiment of the dilator of FIG. 1.

FIG. 7 is an isometric view of the dilator of FIG. 6.

FIG. 8 is an end view of the dilator of FIG. 6.

FIG. 9 is a top plan view of the dilator of FIG. 6.

FIG. 10 is an isometric view of an alternative embodiment of the dilator of FIG. 1.

FIG. 11 is an end view of the dilator of FIG. 10.

In the accompanying drawings, like reference numbers are used throughout the various figures for identical structures.

DESCRIPTION OF THE PREFERRED EMBODIMENTS

Figure 12:
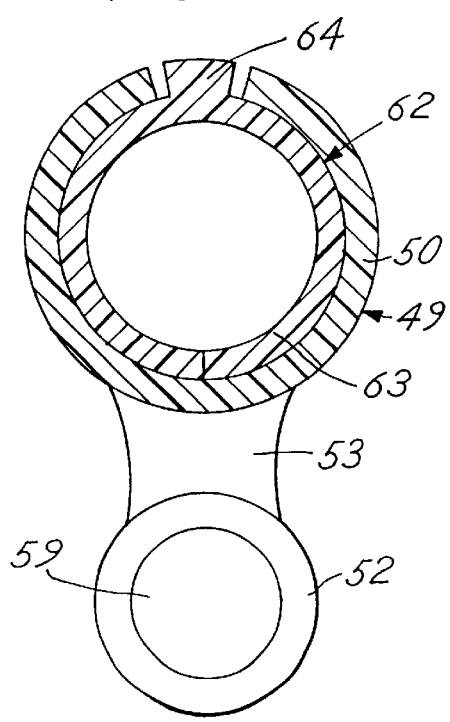
FIG. 12 is a cross-section view of the dilators of FIGS. 6 and 10.

Referring to FIG. 1, a preferred embodiment of a percutaneous dilator 10 of the present invention is depicted. The dilator 10 is a tube 12 having a proximal end 14 and a distal end 16. The tube 12 is typically made from a flexible polymer such as polyurethane. Referring to FIGS. 1 and 2, as preferred, the proximal end 14 defines a slit 18 and an opening 20 for receiving a solid tube, needle or another dilator 10 of slightly larger external diameter than that of the opening 20. Preferably, the slit 18 is formed through the wall 22 of the tube 12 extending longitudinally from the opening 20 along the length of the tube 12 and terminating at the distal end 16. The slit 18 allows for radial expansion of the tube 12 upon the insertion of a slightly larger diameter second tube. It is contemplated that the slit 18 need only extend partially through the wall 22—the remaining wall thickness allowing for radial expansion of the tube 12.

Referring to FIGS. 1 and 3, the distal end 16 includes slit 18, a plurality of slits 24 positioned equidistant around the periphery of the tube 12, and an opening 26. Again, the slits 24 are formed through the wall 22 of the tube 12. In a preferred embodiment, the slits 24 extend from the distal end 16 toward the proximal end 14 to beyond the approximate longitudinal midpoint of the tube 12. As compared with the single slit 18 at the proximal end 14, the plurality of slits 24 allow for easier radial expansion of the dilator 10. As most preferred, four slits are spaced equidistant around the tube's periphery. For the dilators that have the plurality of slits 24 at the distal end, the slit 18 does not need to extend the fill length of the tube 12 as long as there is some longitudinal overlap of the slits to permit sufficient expansion of the dilator. Of course, other numbers, lengths and orientations of slits which allow expansion of the dilator can be used and are considered within the scope of the present invention.

Figure 16:
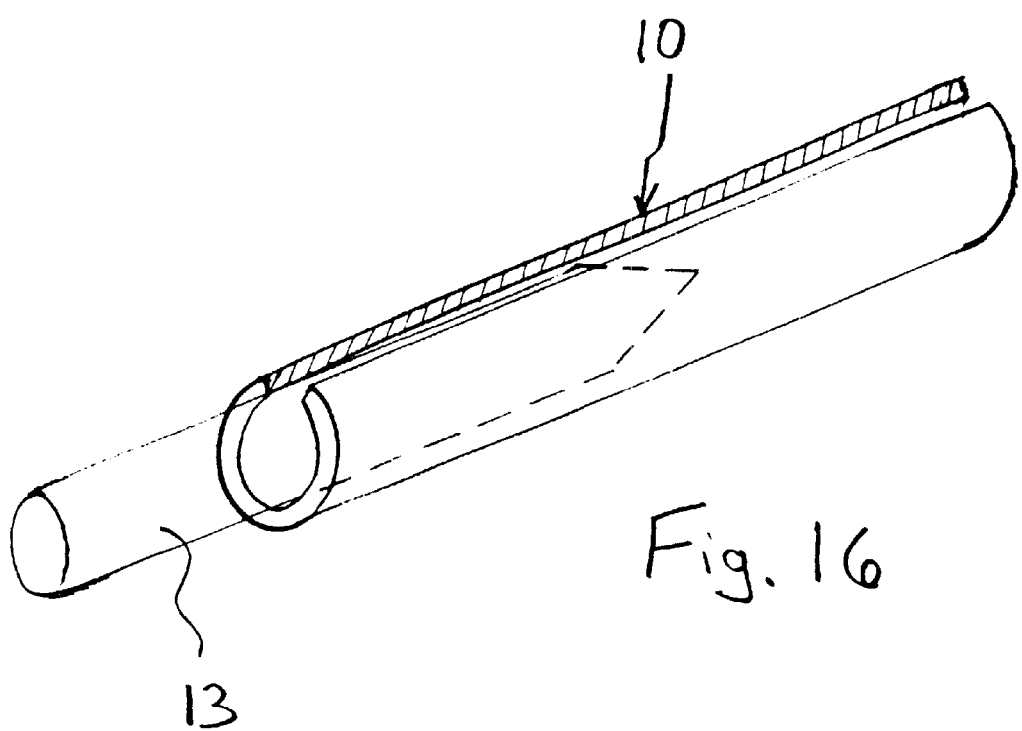
FIG. 16 is an isometric view of a needle inserted in the dilator of FIG. 1.

In a preferred method of use, a solid tube or needle is percutaneously introduced through the skin into the ligamentum flava or tissue of the human body to the desired location, for example, the epidural space. The dilator 10 is then inserted into the lumen of the solid tube or needle. The solid tube is removed leaving the dilator 10 inserted into the ligamentum flava Next, a solid or slotted tube, a needle 13 or another dilator 10, having a slightly larger external diameter than that of the opening 20, is inserted into the tube 12 through the opening 20, as shown in FIG. 16. The slit 18 permits the larger diameter tube or dilator to slide into the tube 12 by allowing for the radial expansion of the dilator 10. As the larger diameter tube or dilator passes through the tube 12 toward the distal end 16, the plurality of slits 24 allow for easier radial expansion of the dilator and consequently easier insertion of the larger diameter tube. The dilator 10 may then be removed leaving the larger diameter tube or dilator in the ligamentum flava at the targeted location. If further expansion is desired and a larger diameter solid tube was inserted into the dilator 10, the entire process may be repeated by inserting another dilator into the larger solid tube. However, if further expansion is desired and a larger dilator was introduced into the dilator 10, a larger diameter tube or dilator need only be inserted into the previously inserted dilator to effect expansion of the access hole. This process can be repeated until the tube that remains in place has the desired diameter to permit the insertion of the larger leads or surgical instruments.

Referring to FIGS. 4 and 5, an alternative preferred embodiment of the present invention is depicted. A dilator 30 is shown having a rectangular shaped cross-section. While a rectangular shape dilator is preferred, other dilator shapes having other numbers of sides may be used and is considered within the scope of the invention. The rectangular shape cross-section of the dilator 30 permits the insertion of a matching rectangular shaped solid tube or dilator. The rectangular shaped solid tube or dilator introduced to the epidural space, for example, allows for the insertion of a paddle type lead having a similar rectangular cross section. The dilator 30 defines an elongated rectangular tube 32 having a proximal end 34 and a distal end 36 and a rectangular opening 38. A slit 40 extends longitudinally along the length of the tube 32 and preferably extends from the proximal end 34 to the distal end 36. A plurality of slits 41 extend longitudinally from the distal end 36 toward the proximal end 34. The plurality of slits 41 are located on opposing walls of the dilator 30. The slits allow for lateral expansion of the dilator 30 upon the introduction of a larger solid rectangular tube or a larger dilator 30 into the rectangular opening 38. As above, by alternating insertion of the dilator 30 and a larger rectangular shaped solid tube or dilator, dilation of the skin, ligamentum flava and other soft tissue will occur, thereby permitting insertion of rectangular shaped leads into the targeted stimulation area.

Referring to FIGS. 6–13, a most preferred embodiment for percutaneous dilation is illustrated and comprises the alternating insertion of an introducer dilator 49 and a cam dilator 62. Referring to FIGS. 6–9, the introducer dilator 49 is depicted comprising an introducer expansion tube 50 having an attached tubular guide 52. The introducer expansion tube 50 includes a proximal end 54, a distal tapered end 56, a slit 58 extending longitudinally along the length of the tube 50, a wedge 60 at the proximal end, and an opening 61. The introducer expansion tube 50 is typically made from a flexible polymer such as polyurethane. The slit 58 permits the radial expansion of the introducer tube 50 when a larger diameter tube or dilator is introduced into opening 61. It is contemplated that a plurality of slits may be positioned around the expansion tube 50 for easier radial expansion. As above, the expansion of the introducer tube 50 effects expansion of the access hole for introduction of larger leads or surgical instruments.

The guide 52 is positioned externally on the introducer tube 50 and defines an opening 59 to receive a surgical guide wire 51 for anchoring of the introducer dilator 49 to the bone 55 in a relatively fixed position adjacent the ligamentum flava 57, as shown in FIG. 6. Alternatively, the guide 52 may comprise a plurality of tubular eyelets positioned externally in longitudinal alignment on the introducer tube 50. Other methods of anchoring the dilator 49 to the bone may be used and are considered within the spirit and scope of the present invention. The tubular guide 52 is offset from the introducer expansion tube 50 and is attached to the tube 50 through the use of an integral support member 53 or other suitable means of attachment.

In use, after a guide wire is drilled into and attached to the bone of the vertebrae, for example, adjacent the targeted stimulation area, the introducer dilator 49 is slid along the guide wire with the guide wire passing through tubular guide 52. The introducer dilator 49 is slid along the guide wire until the distal end 56 of the introducer tube 50 penetrates and extends through the ligamentum flava to the targeted area. Once the introducer tube 50 is positioned, the guide wire and tubular guide 52 hold the expansion tube 50 in place at the targeted location. A solid tube having a slightly larger external diameter than the opening 61 may be inserted into the introducer tube 50 of the dilator 49 effecting expansion of the access hole and allowing for the introduction of larger leads to the epidural space, for example. Alternatively, the cam dilator 62 of the present invention may be introduced into the introducer tube 50 of the dilator 49, as exemplified by FIG. 12.

Referring to FIGS. 10 and 11, the cam dilator 62 is depicted having a slit tube 63, a guide cam 64 and a tapered end 66. The slit tube 63 has a slit 68, located opposite the guide cam 64, extending longitudinally along the length of the tube 63. The guide cam 64 also extends longitudinally along the length of the tube 63. The cam dilator 62 is inserted into the introducer tube 50 at the proximal end 54. Insertion is accomplished by aligning the guide cam 64 with the wedge 60 of the tube 50. As the cam dilator 62 is inserted into the lumen of the introducer tube 50, the guide cam 64 opens the slit 58 causing expansion of the tube 50, as shown in FIG. 12. Once the cam dilator 62 is inserted, the introducer dilator 49 is removed leaving the cam dilator 62 in the targeted location.

Figure 13:
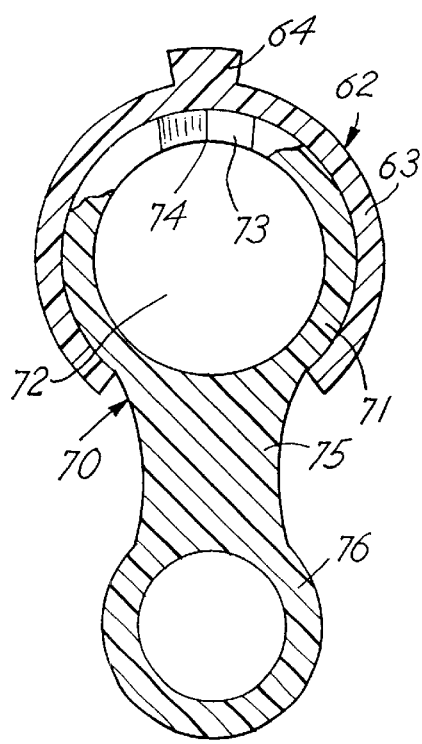
FIG. 13 is a cross-section view of the dilator of FIG. 10 and a larger embodiment of FIG. 6.

Referring to FIG. 13, if further expansion is desired, a larger introducer dilator 70 is inserted into the cam dilator 62 with the guide wire passing through the tubular guide 76. The dilator 70 has a larger expansion tube 71 and opening 72. Again, the expansion tube 71 includes a wedge 73 and a slit 74. The tubular guide 76 is also offset from the expansion tube 71 by an integral support member 75. Through the insertion of the larger expansion tube 71 into the slit tube 63 of the cam dilator 62, the tube 63 is radially expanded effecting expansion of the access hole. The cam dilator 62 may then be removed leaving the dilator 70 in position at the targeted stimulation area. If desired, a solid tube having a diameter larger than the opening 72 can be inserted into the expansion tube 71. Alternatively, the above process can be repeated by inserting a second cam dilator of the present invention into the expansion tube 71 of the dilator 70. Significantly, the above process may be repeated until the desired opening in the ligamentum flava or other soft tissue is achieved while simultaneously maintaining the dilators at the targeted location.

Figure 14:
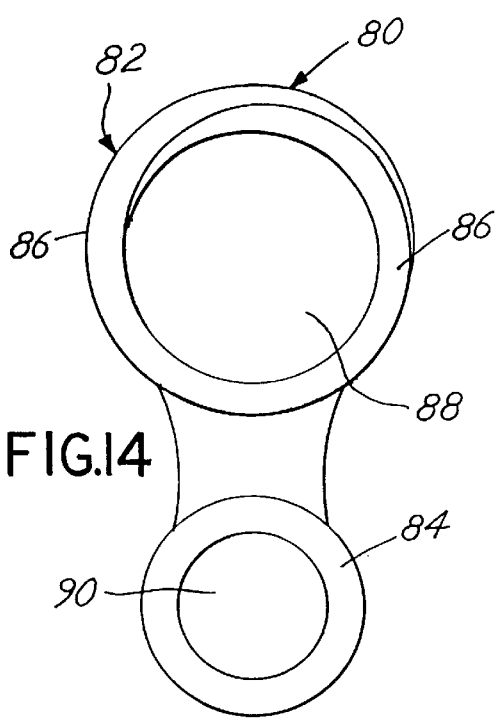
FIG. 14 is an end elevation view of an alternative embodiment of the dilator of FIG. 1.
Figure 15:
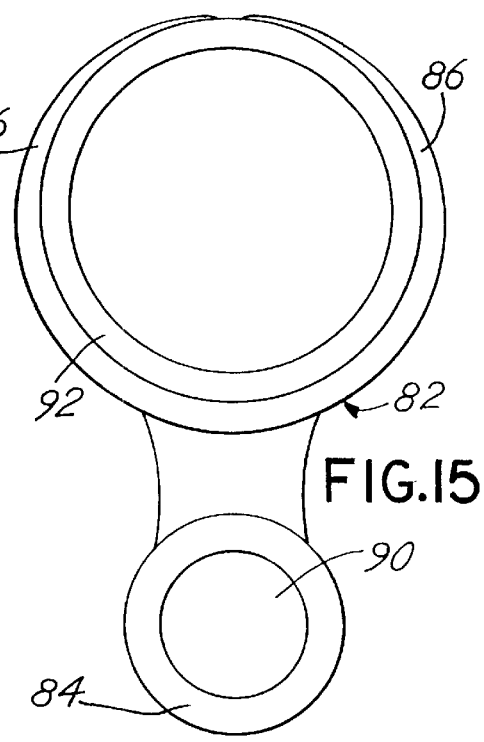
FIG. 15 is an end elevation view of the dilator of FIG. 14 including an inserted tube.

Referring to FIGS. 14 and 15, another preferred embodiment of the present invention includes a dilator 80 defining an offset guide 84 and an overlapping expansion tube 82. The offset guide 84 defines an opening 90 for receiving a surgical guide wire for anchoring the dilator 80 to the bone adjacent the penetration area. The overlapping expansion tube 82 includes a pair of opposing flexible tubular walls 86 made of a plastic material, such as, polyurethane, and forms an opening 88. As depicted, the flexible tubular walls 86 overlap each other and will radially expand upon the insertion of a solid or slotted tube 92 or a dilation tube having an external diameter larger than the opening 88. As preferred, progressively larger dilation tubes are inserted into the opening 88 until a tube of the final desired size is inserted. The final tube serves as the working channel and is left within the expansion tube 82 of the dilator 80 which remains anchored adjacent the penetration area.

The preferred embodiments of the invention are now described as to enable a person of ordinary skill in the art to make and use the same. Variations of the preferred embodiment are possible without being outside the scope of the present invention. Therefore, to particularly point out and distinctly clam the subject matter regarded as the invention, the following claims conclude the specification.

What is claimed is:

1. An apparatus for dilating the ligamentum flava or other soft tissue comprising:
    a first radially expandable dilator having a proximal end and a distal end, the dilator defining an opening and having a plurality of slits spaced equidistant around the periphery of the dilator and extending from the distal end toward the proximal end; and
    a tube having an external diameter larger than the opening in the first dilator, the tube effecting radial expansion of the first dilator upon the insertion of the tube into the opening of the first dilator.

2. The apparatus of claim 1 wherein the slit extends longitudinally from the proximal end to the distal end distal end of the dilator.

3. The apparatus of claim 1 wherein the tube is a second radially expandable dilator.

4. The apparatus of claim 1 wherein a needle effects radial expansion of the first dilator.

5. The apparatus of claim 1 wherein a guide is positioned externally on the first dilator for receiving a guide wire.

6. The apparatus of claim 1 wherein the first dilator is an expandable tube having a rectangular cross-section.

7. The apparatus of claim 6 wherein the rectangular shaped dilator defines a plurality of slits extending from the distal end toward the proximal end, the plurality of slits being located on opposing walls of the dilator.

8. An apparatus for dilating the ligamentum flava or other soft tissue comprising:
    a first radially expandable dilator having a proximal end and a distal end, the first dilator further comprising a first expansion tube and an offset guide connected to the first expansion tube, the first expansion tube defining an opening and having a slit; and
    a second radially expandable dilator defining a second expansion tube and a guide cam positioned externally on the second expansion tube, the second expansion tube positioned within the opening of the first expansion tube with the guide cam inserted into the slit of the first expansion tube, whereby the guide cam of the second dilator effects radial expansion of the first dilator.

9. The apparatus of claim 8 wherein the guide cam is positioned in alignment with the slit in the first expansion tube.

10. The apparatus of claim 9 wherein the first expansion tube defines a wedge located in alignment with the slit in the first expansion tube, the wedge providing easier insertion of the guide cam within the slit.

11. The apparatus of claim 8 wherein the offset guide is connected to the first expansion tube by an integral support member.

12. The apparatus of claim 8 wherein the offset guide is a tubular channel extending along the longitudinal length of the first expansion tube.

13. A method for dilating the ligamentum flava and other soft tissue within a human body comprising the steps of:
    percutaneously inserting a first expandable dilator to a targeted location within the human body, the first dilator defining a first expandable tube having an opening and defining a slit, and an offset guide connected to the first expandable tube, the guide receiving a guide wire; and inserting a second radially expandable dilator into the first dilator, the second expandable dilator defining a second expandable tube and a guide cam, the second expandable tube being inserted into the opening of the first expandable tube with the guide cam inserted into the slit in the first expandable tube, whereby the guide cam effects radial expansion of the first expandable tube.

14. The method of claim 13 further comprising the steps of:

removing the first expandable dilator leaving the second expandable dilator in the desired position within the human body;

inserting a third radially expandable dilator into the second expandable tube, the third dilator defining a third expandable tube having an external diameter larger than the diameter of the opening in the second expandable tube, the third expandable tube positioned within the opening of the second expandable tube, the larger external diameter of the third expandable tube effecting radial expansion of the second expandable tube, the third dilator also defining an offset guide connected to the third expandable tube, the guide receiving the guide wire; and removing the second dilator leaving in place the third dilator in the human body.

15. The method of claim 13 wherein the first expandable tube further defines a slit extending longitudinally along the length of the first expandable tube, and a wedge positioned in alignment with the slit.

16. The method of claim 15 wherein the guide cam is positioned in alignment with the slit in the first expandable tube.

17. The method of claim 13 wherein the guide cam extends longitudinally along the length of the second expandable tube.

18. The method of claim 14 wherein the offset guide is a tubular channel extending along the longitudinal length of the first expandable tube.

19. The method of claim 13 wherein the first expandable tube comprises a plurality of slits for radial expansion.

* * * * *

UNITED STATES PATENT AND TRADEMARK OFFICE
CERTIFICATE OF CORRECTION

PATENT NO. : 6,277,094 B1  
DATED : August 21, 2001  
INVENTOR(S) : Schendel

Page 1 of 1

It is certified that error appears in the above-identified patent and that said Letters Patent is hereby corrected as shown below:

<u>Column 6, claim 2,</u>
Line 19, "the distal end distal end" should read -- the distal end --

Signed and Sealed this

Twenty-sixth Day of February, 2002

Attest:

JAMES E. ROGAN
*Attesting Officer*     *Director of the United States Patent and Trademark Office*